(12) United States Patent
Snook

(10) Patent No.: US 6,193,371 B1
(45) Date of Patent: Feb. 27, 2001

(54) KERATOMETER/PACHYMETER

(76) Inventor: Richard Snook, 3856 W. Argo St, Tucson, AZ (US) 85742

( * ) Notice: Subject to any disclaimer, the term of this patent is extended or adjusted under 35 U.S.C. 154(b) by 0 days.

(21) Appl. No.: 09/534,979

(22) Filed: Mar. 27, 2000

(51) Int. Cl.$^7$ ........................................ A61B 3/10

(52) U.S. Cl. ............................................. 351/212

(58) Field of Search ........................... 351/205, 206, 351/208, 210, 211, 212, 214, 219, 221, 246; 606/4, 5, 166

(56) References Cited

U.S. PATENT DOCUMENTS 4,838,682 * 6/1989 Portnoy ................................. 351/212
6,033,075 * 3/2000 Fujieda et al. ........................ 351/212

* cited by examiner

Primary Examiner—George Manuel
(74) Attorney, Agent, or Firm—Robert J. Schaap

(57) ABSTRACT

A video Keratometer/Pachymeter comprising an array of illuminated points disposed in concentric circles around the optical axis of a television camera for definition of corneal surface contour by a method similar to the well know Placido, except that the isolated point ring format provides unambiguous back ray trace information to eliminate errors inherent in the prior art, in combination with a projected pattern of discrete points to elicit Tyndall images for definition of both anterior and posterior corneal surface by triangulation using multiple television cameras viewing the reflected and Tyndall images, substraction of a view of the eye with neither pattern superimposed as well as each pattern in sequence for isolation of the data containing points from the general clutter of background pictorial information.

25 Claims, 6 Drawing Sheets

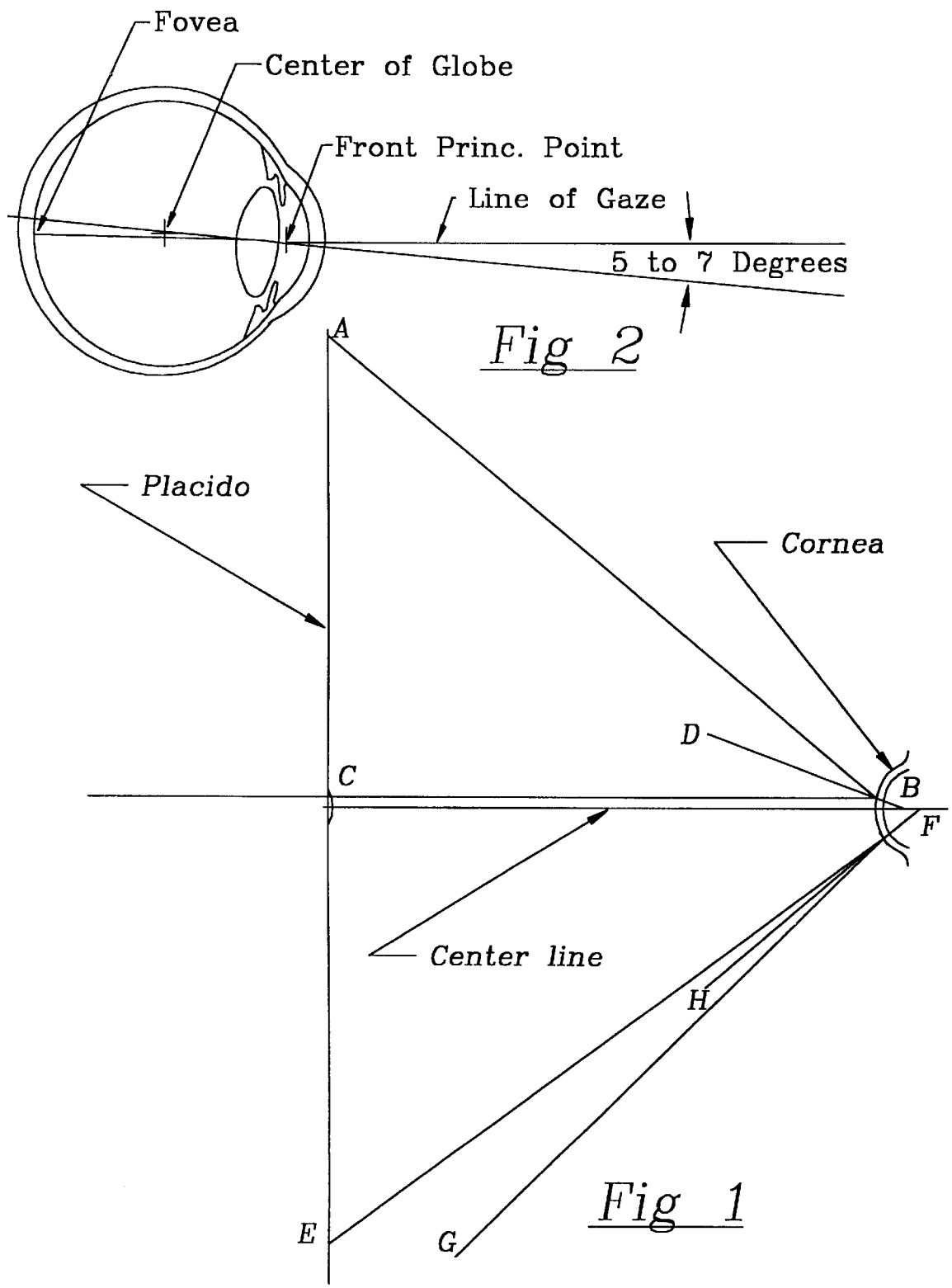

KERATOMETER/PACHYMETER

BACKGROUND OF THE INVENTION

1. Field of the Invention

The present invention relates to improvements in the art of photo-keratometry and pachymetry and, more particularly, to the use of television techniques to ascertain the contour and thickness of the cornea. More specifically, the present invention relates to improvements in the art of photogrammetry where the reflection of a placido or other illuminated target by the surface of the contact cornea is analyzed to determine the surface contour and analysis of steroscopic images of point type Tyndall images for establishing thickness of the cornea. A pachymeter is an instrument for measuring the thickness of the cornea, commonly by ultrasound or optical devices. A keratometer is an instrument for determining the shape of the corneal surface which often uses a placido or other illuminated target which is reflected from the surface to be characterized for surface contour. The present invention measures both the keratorefractive surface shape by a modification of Placido's device coupled with a photo triangulation Tyndall image analysis method for determining the corneal thickness.

2. Brief Description of Related Art

Placido's method as applied to corneal surface measurements dates from the middle of the last century through the early thirties when the Zeiss optical company of Germany introduced a "Photo Keratoscope" designed by Amsler of Lausanne Switzerland. In general, the art has required the image reflected by the eye to be photographed and the image on the film measured in a second step to derive the data from which the contour map is generated. Initial development of keratometry came from Helmholtz in 1854, Placido published an article in 1880 "A Novo instrumiento par analyze immediate das irregularidades de curvature de cornea" Periodico Ophthalmol Practica 1880;6:44–49. Gullstrand expanded the basis for the present invention in his "Photographisch-Ophhthalmometrische und klinische Untersuchungen uber die Hornhautrefraktion"(from Ludlam translation Am.J. Optom. 1966;43;143–198). In 1896, Gullstrand disclosed the foundation for the current photographic based technology but his apparatus had no provision for automatic data assessment and was limited to a four millimeter diameter zone. As a result, multiple exposures and calculations were necessary to map the corneal surface.

A more recent attachment for the ubiquitous Bausch and Lomb keratometer is the Topogometer produced by Soper Brothers of Houston, Tex. This device provides a series of fixation points for the patent to look at which permits largest areas of the cornea to be described. This method is inaccurate because the calibration assumes spherical surfaces or aspheric surfaces centered on the image center of the instrument. Because the corneal surface is aspheric even in the normal cornea, this multiple fixation technique produces errors which are a function of point of gaze but which are undefinable.

U.S. Pat. No. 3,797,821 discloses the use of a camera to record the placido reflex from a patient's eye. From this photograph, the radius of surface of curvature of the cornea is determined at several points is calculated using a complex computer system. The use of a ground glass focusing screen with the small aperture of the optical system and large linear magnification makes use difficult and requires a darkened room for operation. Additionally, the method utilizes a separate video/computer analysis step which further degrades accuracy, speed and increases cost of operation.

More recently, U.S. Patents, such as U.S. Pat. No. 5,841,511 to D'Aousa, et al, have addressed the problem of the inherent ambiguity of the concentric circle form of the Placido while U.S. Pat. No. 5,847,804 to Sarver, et al attempts to define the corneal apex through the use of an additional camera which purports to locate the apex and limbus. In fact, these do provide some enhancement of the basic technique from the last century, but they fall short of the goal of exact definition of corneal surface shape and cannot provide thickness information which is imperative for many surgical procedures.

U.S. Pat. No. 4,440,477 discloses a method and device for measuring the corneal surface, comprising a slit lamp for illuminating the corneal surface, a camera for recording the reflection from the corneal surface, and a processor to calculate the image distance and the radius of curvature of the eye. the operation of the processor is not detailed in U.S. Pat. No. 4,440,477. Additionally the prior art devices do not work well in the presence of reflections from objects or lights int he room and do not provide rapid, accurate measurements such as are required fro modern contact lens fitting. Consequently, the systems are costly, complex, slow and difficult to change if required.

The traditional approach to photogrammetry has bene very software intensive and, thus, quite costly. The most common technique is to convert the entire television image to digital form prior to sorting, calculating by matrix algebra techniques, and display. The digitized image must occupy only a portion of the available memory in any computer system if there is to be the capacity to act upon the image information. More recent technique is described in my U.S. Pat. Nos. 5,110,200, 4,412,965, as well as Gersten's work such as disclosed in U.S. Pat. No. 5,384,608. The present invention addresses some of the problems found with the prior art.

Placido based instruments are the most common of the keratometric instruments of the prior art. Inherent in the Placido system are several assumptions which have a bearing upon the accuracy of the measurements. Among these assumptions are:

1. The corneal contour can be defined accurately from reflected concentric circles on the tear film covering the cornea.
2. The Placido image plane and location of the corneal apex are know.
3. The measurement of anterior surface curvature in dioptric terms is an accurate measure of the focusing power of the eye.
4. Valid data can be obtained from very small reflections near the center of the reflection of Placido's disc.

When photographs of the reflections of Placido's disc are made the contour of the cornea is such that only the middle zone can be measured since the more peripheral zone is sloped in such a way as to prevent the reflected image to be seen to be a centrally located camera. The central zone is not resolved because the size of the reflection approaches the inherent resolution of the camera employed and the error of determination increases to infinity at the center of the image being analyzed. Measurements of the ring reflections by back tracing rays assumes that the exact point of origin of a ray from a continuous line can be made which is clearly not possible. Because there is no possible measurement at center, even if the reflection of a fixation target is assumed to define the corneal apex, the exact location of the image plane behind the corneal surface and the true apex are unknown. However, both of these must be known for accurate measurement results. Back tracking rays can define the tangent slope of points on the cornea to a fair degree of accuracy, but only if the initial point used in the constructing the surface model is known which is not possible in simple Placido based designs. A keratometer based on Placido's method can only measure anterior surface curvature in terms of radius of curvature at selected points. Because the posterior surface of the cornea in conjunction with the aqueous film constitutes a negative lens, the effective dioptric power is the algebraic sum of the two "lenses". For the keratometric measurement to be strictly accurate, the corneal thickness must be constant, known and perfectly concentric on both the anterior and posterior surfaces. For example, the common Bausch. & Lomb keratometer used in most clinical settings uses a biased value of index of refraction in the conversion from radius of curvature to dioptric form to compensate for this problem. My recent U.S. Pat. Nos. 5,885,767 and 5,735,283 describe apparatus and method for determining the needed information but have an inherent limitation caused by distortion of the projected image points by both surface slope and corneal thickness at the point of reflection.

BRIEF SUMMARY OF THE INVENTION

The present invention employs a pseudo-Placido composed of concentric circles of illuminated points coupled with the projection method of my more recent patents. The location of both the apex and center of optical symmetry are easily defined by triangulated projection of a matrix of points to provide a basis for correction of the inherent errors in the reflected image. Then, the reflected image can be back traced using the known points defined by the pseudo-placido scheme. The local tangent slope derived from the reflective system can, in turn, be used to remove one of the distortions of the projected spot images which leaves only the thickness induced change of shape to be analyzed for pachymetric analysis. The advantage of measurement to center and to the limbus is coupled with full surface thickness data for mapping in the conventional way. In the preferred embodiment, the display of the derived data is in graph form for ease of assimilation and application by the user. This is by means of conventional display algorithms and techniques which are machine dependent and will not be discussed in detail.

The present invention represents a significant improvement in the state of the art while recognizing the stated limitations inherent in the prior art devices.

Accordingly, there is provided herein a new teaching for video image analysis that provides lens or cornea topographical maps of the surface contour and thickness with almost instant display of the data for clinical use.

The improved photo keratometer/pachymeter of this invention comprises: an illuminated target or so-called placido formed of a plurality of small circular illuminated points, preferably disposed in concentric circles around the optical axis of the instrument, which are reflected by the surface to be examined, a television camera and lens system mounted by a modified bean splitter assembly to obtain the image of the surface being examined, a projection system for providing a plurality of Tyndall images in essentially circular form, plural television cameras for capturing the reflected and projected image elements for analysis defined, a conventional electronic computer to derive the surface contour of the eye and to generate the display of the derived shape information for use, and a computer display and a system for aligning the optical axis of the eye with the measuring axis of the instrument.

The video output for general use and recording may be obtained from the present invention, if required. The keratometer/pachymeter system of the present invention makes use of a "bus-card" in a PC type microcomputer to provide fast and accurate measurements without the apparatus associated limitations of the other available systems. With careful use the system will consistently provide information to the lens manufacturer or optometrist to quantify surface shape of contact lenses in addition to measurements of the cornea. Several computer generated data display formats can be made available from a numerical axis and magnitude scale in the eyepiece to computer monitor displays such as a vector map with a line indicating both axis and magnitude against a series of concentric circles representing cylinder magnitude to permit rapid assessment of astigmatism and to permit the user to select a lens which will result in the best corrected vision for the patient. The preferred configuration provides a small hand held device with connection to an external computer.

BRIEF DESCRIPTION OF THE DRAWINGS

Figure 3:
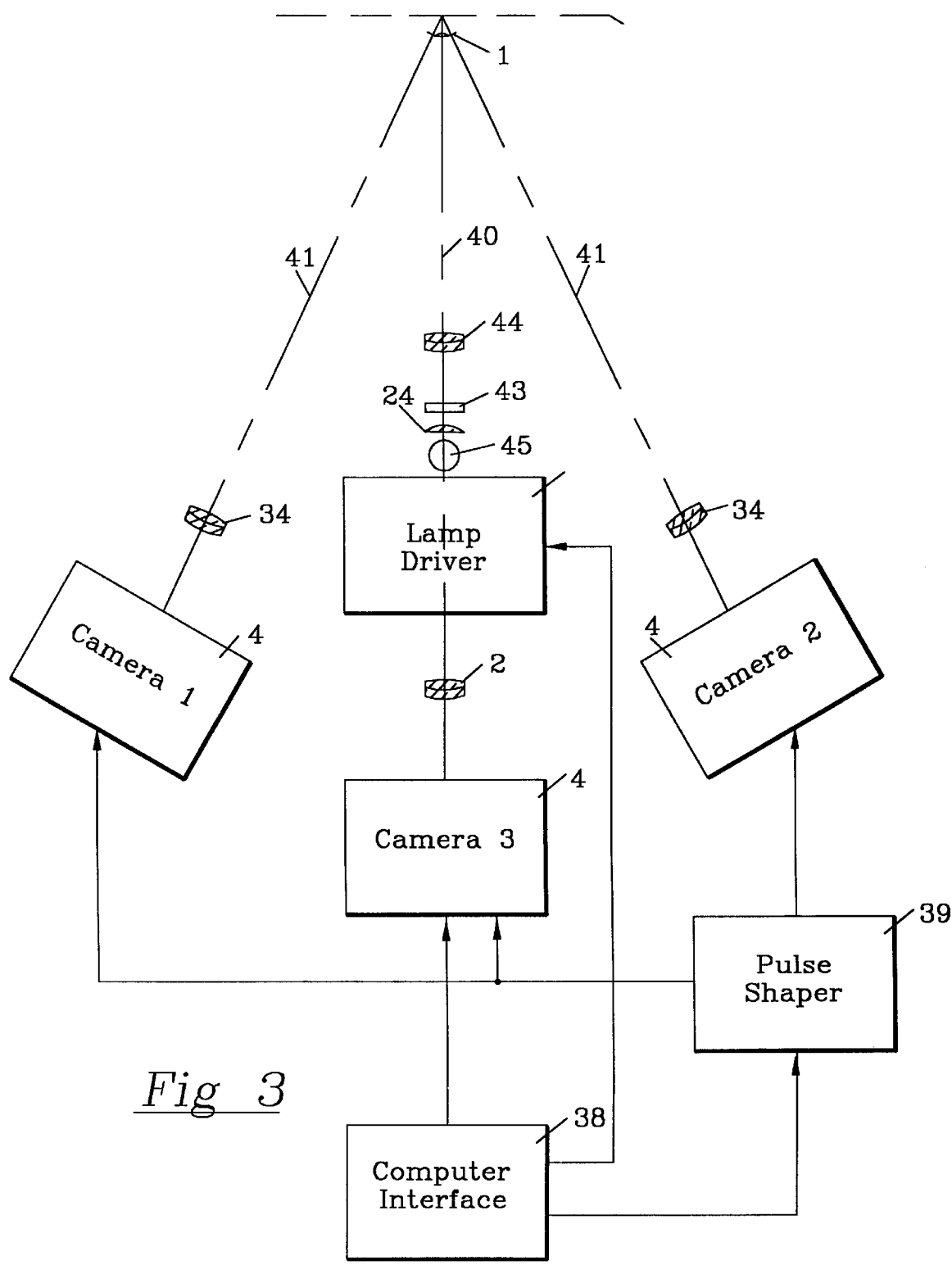
Figure 4:
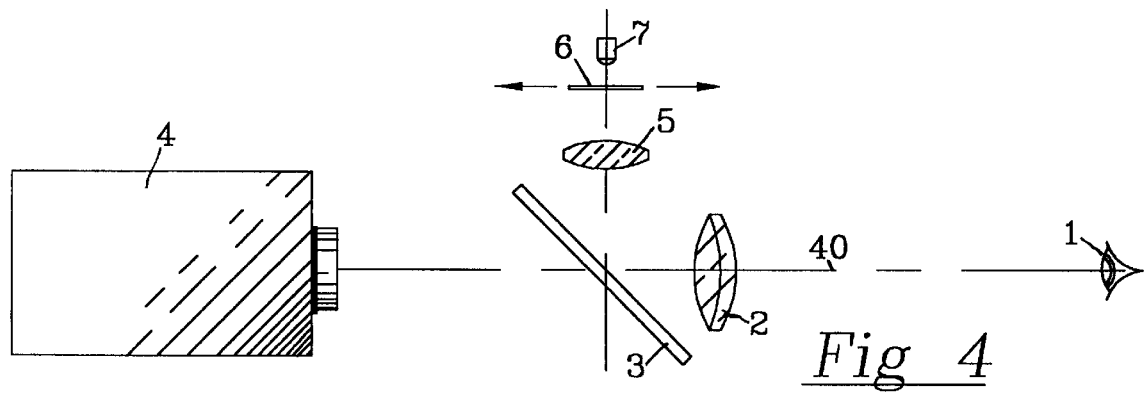
Figure 5:
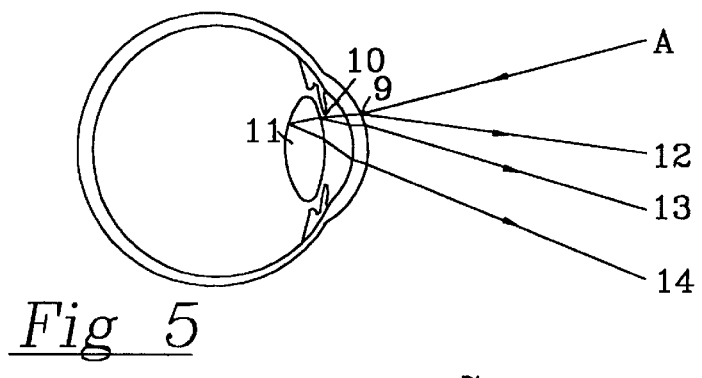
Figure 8:
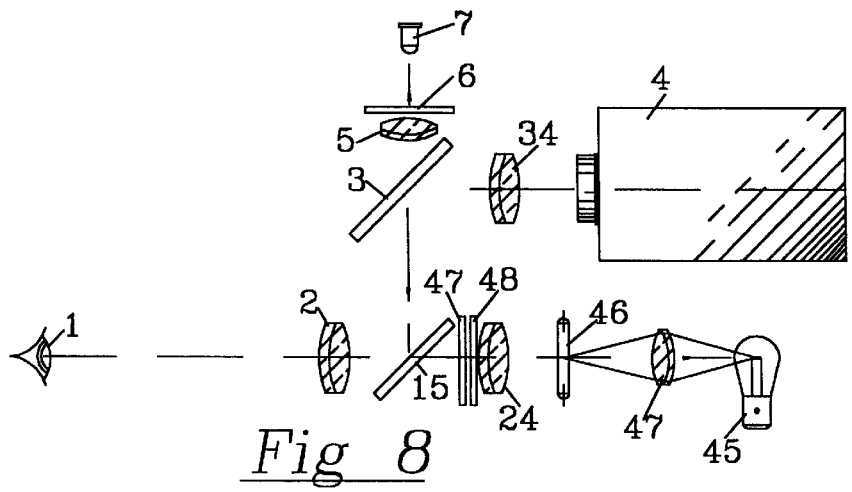
Figure 7:
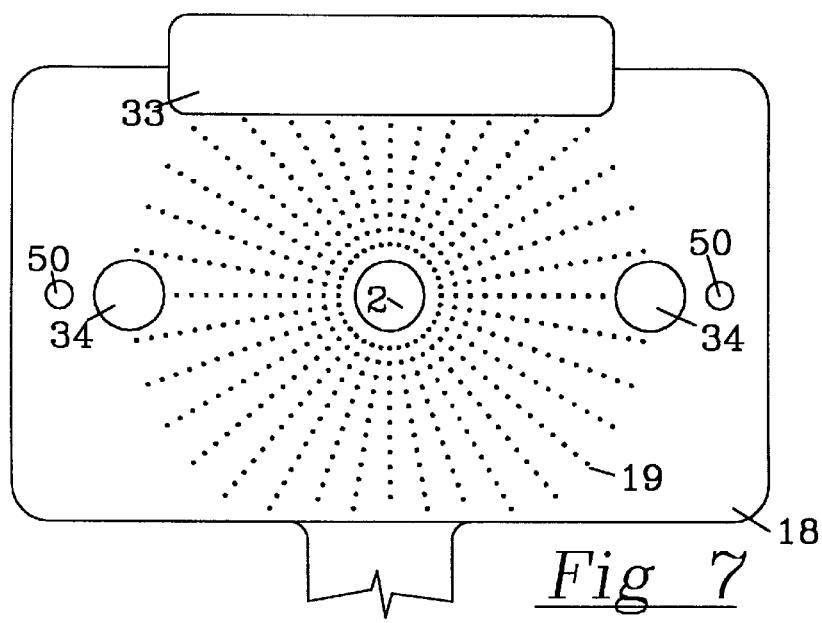
Figure 6:
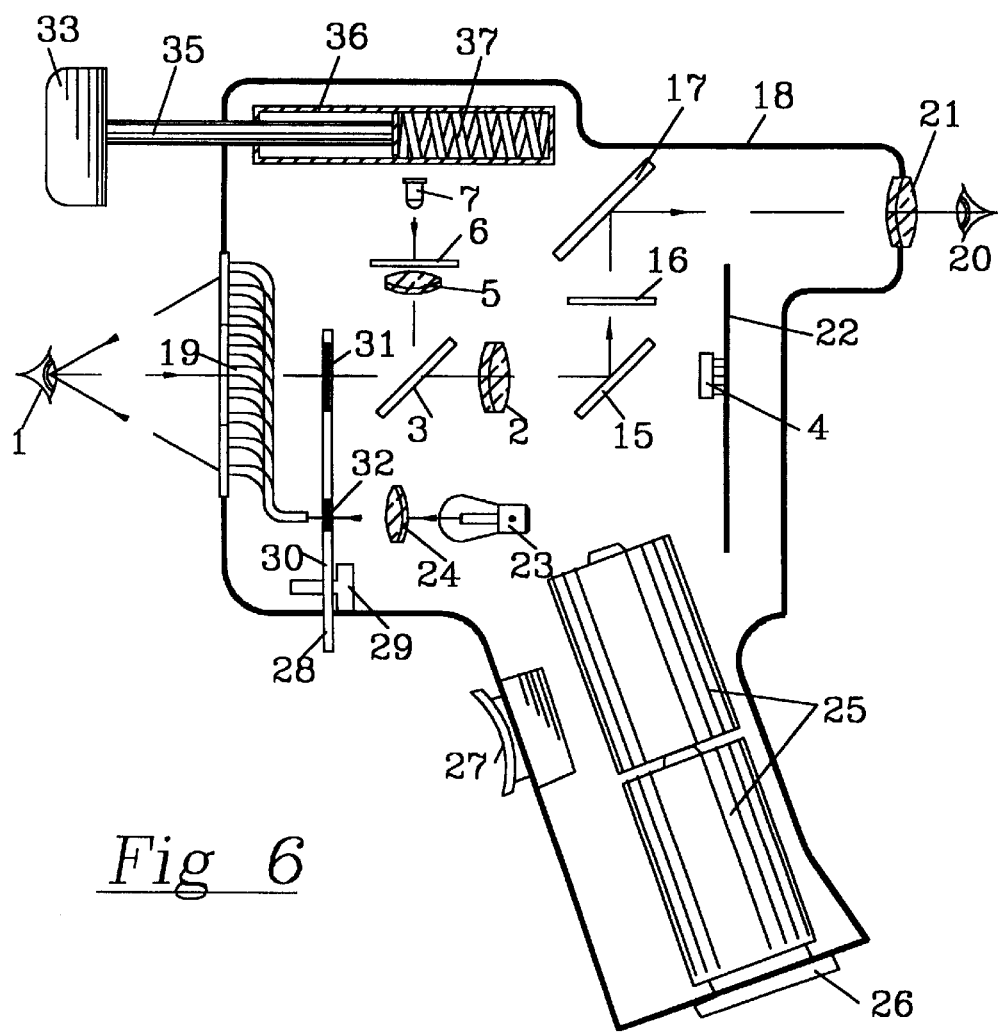
Figure 9:
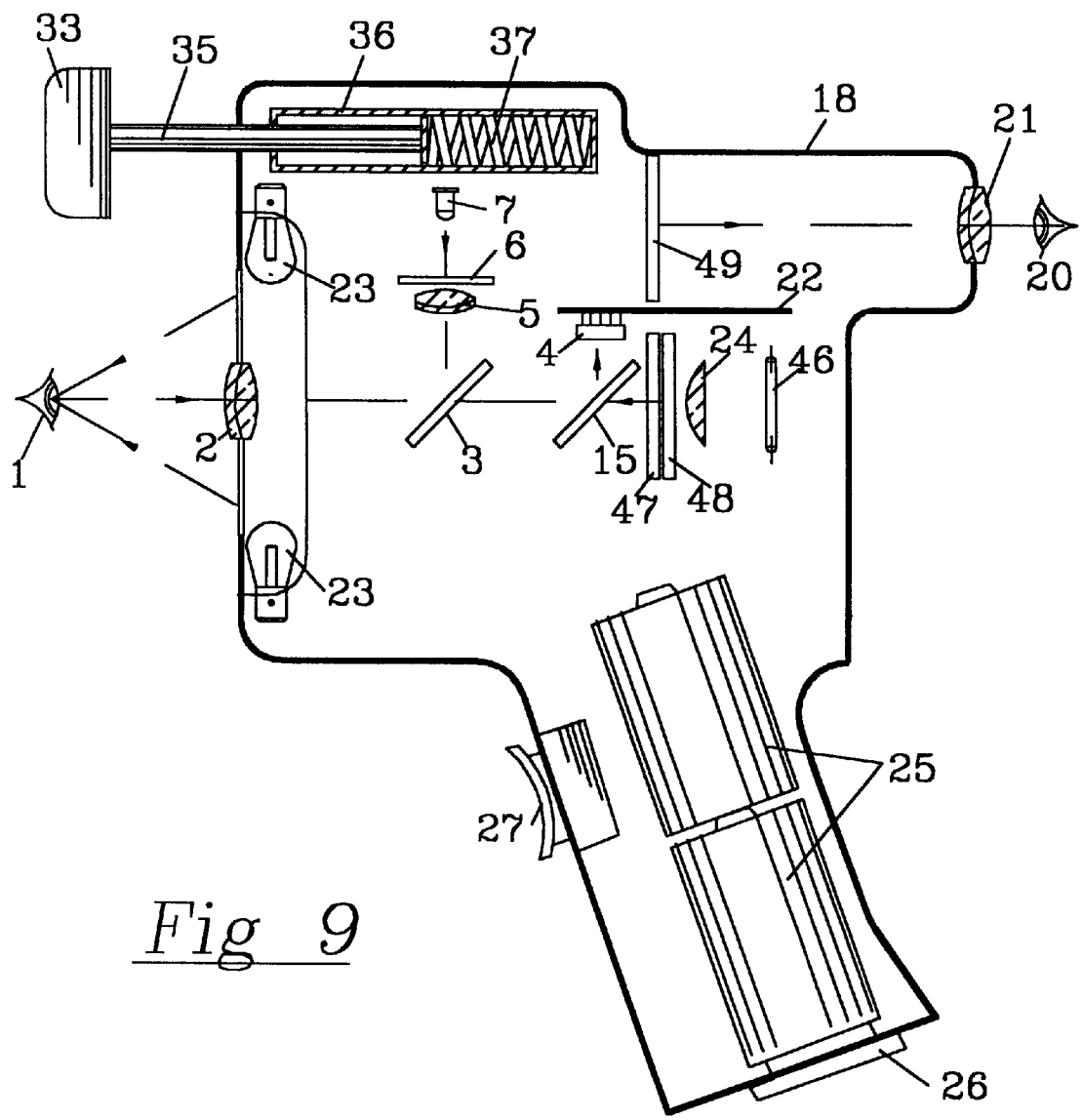
Figure 10:
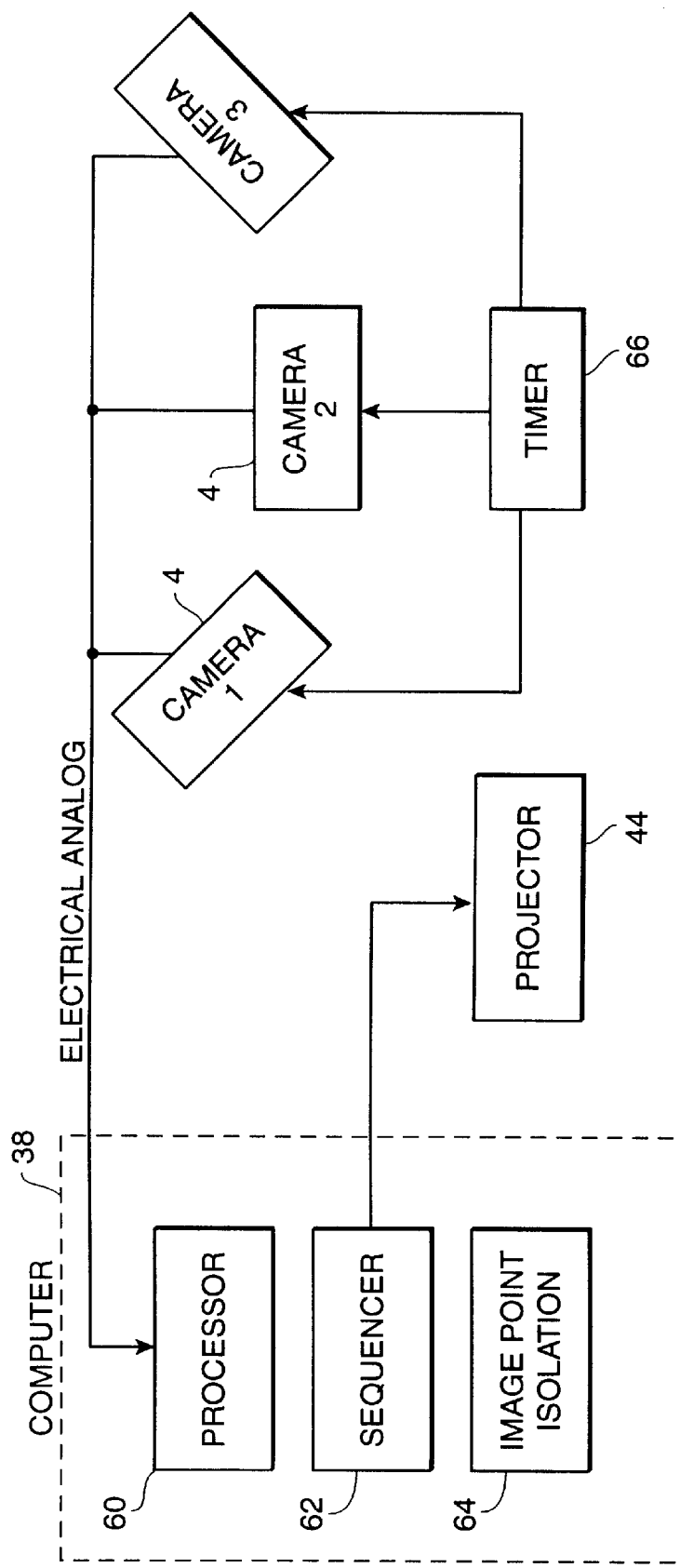

Having thus described the invention in general terms, reference will now be made to the accompanying drawings in which:

FIG. 1 is a schematic view which illustrates the limitation of peripheral measurement of Placido's method;

FIG. 2 is a schematic representation of the eye showing the difference between the line of gaze and the optical centerline of the eye;

FIG. 3 is a block diagram of the major elements of the present invention;

FIG. 4 depicts the movable fixation target employed in the system of the invention;

FIG. 5 shows the raypaths for generation of Purkinje images in the eye;

FIG. 6 illustrates a cross sectional view of one embodiment of the invention;

FIG. 7 is a partial front view of the instrument of the invention;

FIG. 8 illustrates the projection illumination system in the instrument of the invention;

FIG. 9 is a cross sectional view of the preferred embodiment of the present invention; and FIG. 10 is a schematic block diagram showing some of the major components forming part of the circuit used in the system of the present invention.

DETAILED DESCRIPTION OF A PREFERRED EMBODIMENT

Referring now in more detail and by reference characters to the drawings, and presently to FIG. 2, there is a small area of the retina there is a concentration of the cone type photo-receptor cells which are synapsed on an almost one to one ratio with nerve fibers. This central vision area is termed the fovea. It is at the fovea that the critical vision associated with reading and similar optical tasks takes place. The optical axis of the eye does not coincide with the fovea, but rather is displaced by five to seven degrees. The main light focusing power of the eye is contained in the cornea and the fluid filled anterior chamber in front of the crystalline lens. The surface curvature and thickness of the cornea determines the effective focal length of the optical system and deformation from ideal form results in reduced visual acuity if uncorrected by spectacles, contact lenses or surgical intervention. The lens is mounted in a network of zonules or fibers connected to a muscle system which permits the eye to accommodate for image plane position to clear focus of objects at various distances. The curvature of the front of "anterior" surface of the cornea is the most important single element in the optical system of the eye and the contourometer of this invention is designed to provide a systematic measurement of this curvature.

The anterior surface of the normal cornea is not quite spherical, as is assumed in the construction of many of the prior art devices, such as the Bausch and Lomb Keratometer, but more nearly is an evolute ellipsoid. The central two or three millimeters of the normal cornea does conform reasonably to the spherical form so the simplistic model will serve to illustrate the optics of the system for rays at or near the common optical axes.

FIG. 1 illustrates one of the principal limitations of Placido based measurements. The focal length of a convex mirror is one-half of the radius of curvature and the image and object sizes can be related to the focal length. The object in this case may take the form of a placido or Placido's disc. The placido is commonly in the form of a trans-illuminated surface of translucent material with opaque concentric rings. The target is illuminated by one or more lamps placed behind the disc surface so the translucent areas are bright circles as viewed by the subject. A simplified ray trace is shown where a known point on a circle, A is reflected from the cornea along a part ABC which enters the camera lens located at C. A surface normal at the point of reflection will form equal angles and DBC and an extension of the bisector from D will intersect the axis at some point, If, however, the peripheral cornea has a surface slope, as shown, the ray from some point E will be reflected along a path EFG which will not enter the lens of the camera. Consequently, peripheral areas of the cornea cannot be measured by this technique.

A television camera with adequate sensitivity and resolution is installed by means of a conventional beam splitter and camera mount attachment to the bio-microscope to generate the electronic image of the reflection to be analyzed.

It is obvious that as the angle of the reflection relative to the optical axis increases, with an object size increase at a fixed distance, the amount of deviation from the paraxial computation must also increase at a faster rate. That is to say that the angle subtended by each successive placido ring is not constant. To provide for this optical aberration induced error of calculated curvature of the cornea, a table is used to compensate the calculation for the amount of curvature and the object size, and consequently, angles from the eye surface to the optical axis. It follows that the table value must be a compromise in that the image must subtend a finite width to be visible and, in consequence, the various portions of the image are displaced by slightly different amounts. The table values are derived from measurements made from spherical objects of known diameter. The derived data are in the form of spherical equivalent curvature at the various distances from the assumed optical center and as such are not strictly a true surface shape. The keratometer of common use measures two perpendicular meridians at each selected angle and produces data in the form of "K1,K2", Cylinder and axis. These terms refer to the average dioptric curvature in the two axes which have the greatest and least curvature, assumed to be 90 degrees apart or, "regular" astigmatism. The magnitude of the difference between K1 and K2, and the angle relative to the horizontal of the larger of the two are terms which are commonly used and are recognized by the user as definitive of these descriptive elements, as derived by conventional keratometry. The axis can either be measured or assumed to be regular (90 degrees apart) in the case of contact lenses where the astigmatic curvature is, in general, mechanically generated as a toric or spherical section only.

Referring now to FIG. 2, the so-called Purkinje images are simply reflections of a small fraction of the incident light at each interface where there is a change of index of refraction of the media through which light passes. If the ray enters along the axis of rotational symmetry, all of the surfaces encountered would be exactly perpendicular to the ray path and the reflections would be coincident when viewed along the line of propogation. If, however, the ray A enters at some other angle, the existing reflected light would follow different paths from each interface. When the ray from A strikes the corneas 9 at an oblique angle, the reflected ray would travel along a different path 12. A majority of the light would continue through the cornea and again be slightly deflected before reaching the anterior surface of the lens 10 where the existing reflection would be along a different path 13. Again, the bulk of the light would pass into the lens and at the posterior surface there would be another reflection along a path 14 different from the previous exit paths. While the existing rays also produce internal reflections at the interfaces, the amplitude of these secondary reflections is quite small and probably not visible in a television image. The reflection from the posterior surface of the cornea is often masked by the front surface reflection since they are very close together when viewed and illuminated from the front. The location of the Purkinje reflex from the anterior surface of the lens 13 is variable depending on the state of accommodation and it is desirable that the subject fixate on a point at a considerable distance to inhibit the focus reflex. In the present invention, the fixation target is imaged at optical infinity for this reason. The measurement of anterior chamber depth can only be valid when the subject is not accommodating and so the design of the fixation target system is structured to inhibit the focus reflex.

Turning now to the block diagram, FIG. 3, a computer 38 of the conventional design which may be remote rom the instrument provides control, timing data acquisition, analysis and display for the system. Three television cameras 4 are disposed to provide coincidence of their optical axes at a defined point slightly behind the expected location of the eye to be measured 1. Cameras 1 and 2 provide oblique views at equal angles, preferably thirty degrees from the optical axis 40 of the central camera, camera 3. These cameras provide a stereoptic view of the eye and any reflected or projected pattern thereon for defining the location in three space of the projected or reflected pattern elements. The central camera, camera 3, provides an axial view for the typical Placido type pattern analysis and also serves as a viewfinder to permit the operator to bring the Purkinje reflections into total or near coincidence to establish the axial relationship between the eye 1 and the instrument. A pseudo-placido (not illustrated for clarity) is disposed around the projector lens 44 which also serves to provide an image of the eye 1 to camera 34. In addition, the lens 44 allows projection of a reticle 43 illuminated by a lamp 45 and a condenser lens 24 for projecting a pattern of small spots onto the cornea to elicit the Tyndall images from diffuse reflection within the bulk of the cornea. In operation, the projector lamp 45 and the Placido illuminating lamp are extinguished while the operator positions the instrument against the head of the subject with centering of the image of the eye 1 to be examined and the fixation target positioned to bring the Purkinje reflections into coincidence.

Reflections from the several optical surfaces of the eye were first described by Purkinje in 1823 ND Sanson in 1837.

During an eye examination, these catoptric images are formed at each optical discontinuity when the eye is illuminated with an ophthalmoscope of either the direct or indirect type. They are akin to the reflections used for centering and aligning the several elements of an optical system. However, the bright reflection from the anterior surface of the cornea, actually the tear film on the corneal surface, is much brighter than the reflections from more posterior surfaces. This is due to the large step change in refractive index at the surface from air to the tear film with a R.I. of about 1.334. In order to see the more distant dimmer reflections, the focal illumination system is offset from the viewing axis. The image of the filament of a small bulb is reflected either by a small mirror or a prism located just below the viewing axis of the instrument. All of the common clinical viewing instruments, such as the slit lamp, direct and indirect ophthalmoscopes, and surgical microscopes, are constructed with slightly off axis illumination so that the bright reflection of the illumination source does not mask the other central reflections and more posterior Purkinje reflections. From the observations made with these instruments, the physician is taguth that the so-called "Purkinje images" cannot be superimposed.

The images from the television cameras are in exact temporal synchronism through the action of the Pulse Shaper 39 from a computer providing timing signal complex. This assures that all of the television information is free of motion artifact. The three most recent frames of this background image series are always placed in rotating storage in the computer. When the operator has aligned the instrument and fixation target, he operates a switch to initiate data gathering. On the next vertical blanking interval, the placido illumination lamp is illuminated for a short time to generate three simultaneous pictures of the reflections from the cornea. These are converted to digital format and stored in another location in the computer memory for analysis. At the time of the next successive vertical blanking pulse, the Placido illumination is off and the projection lamp 45 is flashed in synchronism with the television camera control to provide an additional trio of images for analysis. The image data are amplitude normalized in the computer and the averaged value of pictorial information from the three frames, prior to operation of the start switch, are subtracted on a pixel by pixel basis from the second and third exposures with different illumination. The result of the subtraction and thresholding is to remove any pictorial information from the two sets of data containing exposures. This process is disclosed in detail in my other U.S. Pat. Nos. 5,735,283 and 5,886,767.

In order to align the instrument axis with the axis of best symmetry of the eye provision is made for adjusting the location of the fixation target relative to the optical centerline of the instrument. As the subject focuses on the fixation target, any displacement of the target will cause movement of the eye relative to the optical axis of the instrument. As the operator monitors the Purkinje images he manipulates the fixation target position in the instrument which causes the eye to rotate in such a way as to bring about the desired alignment, FIG. 4 illustrates the operation of this feature of the present invention. The optical axis of the camera 4 and the eye 1 are not initially aligned. The image of the eye 1 is centered in the image by positioning the entire instrument relative to the subject's head and brought into proper focus by axial movement of the instrument relative to the subject. The subject is then able to see the fixation target at optical infinity through the action of the lenses 2 and 5. While monitoring the Purkinje reflections, the operator moves the target 6 illuminated by a lamp 7. The viewing path 40 by way of a beam splitter 3 permits simultaneous viewing of the eye 1 by the operation and the fixation target 6 by the subject. As the operator manipulates the fixation target control, the target 6 moves in the focal plane of the lens 6 and the line of gaze of the subjec's eye 1 is caused to move in a corresponding manner. At some point, the dispersion of the Purkinje reflections are observed to be at a minimum indicating that the optical axes of the eye 1 and the camera 4 are coincident. At that time, the operator presses the switch initiating the lamp control sequence and attendant capture of the data containing image sets for computer analysis.

FIG. 8 illustrates the relative location of the major optical elements in an alternative embodiment of the present invention. A television camera 4 with an associated lens 34 is disposed on the folded optical axis of the instrument. Through the action of a pair of beam splitters 3 and 15 the erect magnified image of the eye 1 being examined is focused on the photo sensitive matrix of the camera 4 by positioning the entire instrument relative to the subject. An alignment reticle and/or split image rangefinder prism (not illustrated) of conventional design may be included in this optical path if desired to facilitates the alignment and focus step. After alignment of the instrument and the fixation target 6, the operator presses a switch and the associated computer causes the strobe tube 46 to be fired in temporal synchronism with the television timing signal. The very short illumination time provides a motion artifact illumination of a pattern of points on a reticle 47 which is imaged at the cornea of the eye 1. This image is captured by the associated computer system by well known apparatus and method for producing a digital record of the eye 1 with the pattern superimposed. A filter 48 which is transparent to near infrared light from the lamp 45 prevents disturbing light to be visible to the subject while still providing adequate illumination for the camera 4 which is sensitive to those wavelengths. An additional incandescent lamp 45 is imaged at the center of the strobe tube 46 by a condenser lens 47 so that either lamp may provide the illumination for the system. This permits the operator to select the second illumination system for judging the alignment of the instrument. The central location of the camera 4 provides an undistorted view of the reflection of a pseudo-placido system reflected by the corneal surface of the eye 1 to obtain the conventional Placido type data in the sequence of operations initiated by the user. The illumination of the Placido is also by a strobe tube (no illustrated) so that the sequence of timing may be controlled by the associated computer. Clearly it will be obvious to one skilled in the art that a mechanical shutter system may also be employed for the sequential illumination of the placido and reflected target.

FIG. 6 illustrates the general arrangement of the preferred embodiment. The instrument is contained within a unitary housing 18 provided with a handle which may serve to contain batteries 25 for providing electrical power for operation of the instrument. The batteries 25 may be replaced via a removable cover 26 of conventional design. A brow rest 33 is contoured to rest against the forehead of the subject. In operation, the user places the brow rest 33 against the surface of the forehead of the subject and, by applying pressure on the handle, causes the support shaft 35 to compress a spring 37 located within a suitable housing 36. The shaft 35 may be provided with a hinge or other compliance member so that the brow rest conforms to the contour of the subject's face to eliminate any discomfort to the subject. Small lamps 50 (see FIG. 7) adjacent to the camera lenses 34 illuminates the eye 1 to be examined as the operator moves the entire instrument to cause the image of the eye 1 to be centered in the eyepiece 21. The image of the eye is conveyed to the eyepiece for this purpose by means of beam splitters 3 and 15, a focus aid split image rangefinder plate and prism system 16 and a mirror 17. As the instrument is centered, axial motion will cause the central portion of the image to seem to merge through the well known action of the said rangefinder prism.

By further reference to FIG. 6, it can be observed that a pivotal sheet 30 is supported on a bearing/switch assembly 29 so that a handle 28 can be manipulated by an operator of the device. The handle can be operated to position a pair of filters 31 and 32 to be located within the optical path. This pair of filters 31 and 32 provides the color of the illuminating light from the lamp 23 and through a condenser 24. In this way, the points to be reflected from the corneal surface are lighted.

Simultaneously therewith, one of the filters 31, which serves as a barrier filter, is placed in the return path to band-stop the reflected light and eliminate direct light through the other of the filters 32 which functions as an exciter filter. As an example, the filter 32 may be a blue filter and filter 31 would be a yellow filter and this combination would be used for florescence to depict only the anterior surface of the cornea coated with a dye.

The switch 29 adjusts the light 23 and the camera exposure to compensate for the losses caused by the existence of the filters 31 and 32 in the optical path. These filters 31 and 32 can also be used to enhance the illumination to balance the brightness of the frame center/edge which falls off quickly from the center in the amount of diffuse reflected light reaching the camera 4.

When the instrument is properly positioned with the image of the eye 1 centered and focused, the operator manipulates a control (not illustrated) of conventional design whereby the fixation target 6 is caused to move in the horizontal plane. At some point the Purkinje images are brought into close or total convergence. At this time, the operator presses the switch 27 to initiate the date acquisition. The television cameras 4 are operating continuously during the alignment phase as well as the data gathering phase of the operation of the instrument and, prior to the operation of the switch 27, one or more images taken simultaneously by the cameras is held in storage in digital form within the associated computer for later comparison with the data containing image sets. After the operation of the switch 27 by the operator, the Placido illumination lamp 23 via a suitable lens 24 and a number of optical fibers 19 causes the illumination of a plurality of small discrete points of known location to be illuminated.

The reflection of these illuminated concentric circles of illuminated points from the surface of the eye 1, together with the image of the eye as illuminated by the lamps 50, is observed by the television cameras 4 and a single frame from each camera is simultaneously captured and stored in the associated computer memory for analysis. On the next subsequent television frame, the Placido illumination lamp 23 is extinguished and the reticle projection lamps, not shown, is illuminated causing another set of simultaneous images to be captured in the computer memory in digital form for analysis.

The pseudo Placido containing date frame information from the television frame is recovered in the computer as is the average of the non-data carrying frame or averaged frames recorded prior to the operator of the switch 27. By a well known process of normalization, substraction and thresholding, the reflections of the plurality of pseudo Placido points is recovered and stored for analysis. By the same process, the second group of television images containing the Tyndall images produced by projection of the reticle 47 image are similarly recovered and stored.

Some of the components which form part of the computer 38 and some of the associated components operable thereby are more fully illustrated in the schematic block diagram of FIG. 10 to show the cooperative relationship therebetween. In this case, it can be observed that the computer 38 comprises, among other operative components, a main processor 60 and a sequencing section, or so-called sequencing means 62, for operating the projector. In this way, the projector can take sequential images. The computer also includes, at least schematically, an image point isolation circuit in the form of an image point isolation means 64 and which isolates the reflected and direct images of the points. It can be observed that the three cameras 4 are also operable in synchronous timed relationship by means of a timer 66 and which may, in turn, be operable from the computer processor 60. It can also be observed by reference to FIG. 10 that the processor receives an electrical analog signal from each of the cameras 4. In this way, the computer receives and processes electrical analog signals of the images from each of the cameras.

In the present invention, the illumination and viewing optical systems are made truly coaxial and a small occluder spot of neutral density filter material is cemented to the reticle used for alignment. This reduces the brightness of the central reflection to the extent that the Purkinje images may be very closely aligned when the instrument is being adjusted to capture the images to be used for map construction. In a paper delivered at the American Association of Ophthalmology meeting in 1998, Dr. T. Turner Ph.D. of Orbtek, Inc. stated that the eye contains de-centered and tilted image forming surfaces and consequently light rays do not traverse the straight lines dictated by the common laws of physics. From his "discovery that the Purkinje images cannot be aligned", he concludes that the optical elements of the eye must be tilted, decentered or both. This opinion is reinforced by the fact that the fovea is not located on the axis of best symmetry of the optical system of the eye so the line of gaze or fixation axis when looking at a distant point source is offset by about six degrees from the centerline of the system. The fovea where critical central vision takes place is offset from the optical axis of the eye by about five degrees so image quality at the fovea is assumed to be defined by the perceived asymmetry of the optics.

Clearly, however, if the image formed at the retinal surface is adequately sharp to resolve the Snellen test figures, the optics system of the eye must be fairly close to rotational symmetry. The eye chart figures devised by Snellen comprises a five by five element matrix of twenty-five square elements which each subtend one minute of arc at the viewing distance of twenty feet or six meters. The limitation imposed on the resolving power of the ametropic eye is the packing density of the receptor cells in the fovea centralis where critical images form the center of our visual field. Electron microscopy shows that the individual cells are about one micron in diameter and are packed in a nearly hexagonal manner. From this it follows that the choice made by Snellen was a rational one. Using classical Airy-Rayleigh relationship analysis of the image of a distant point source, light at a wavelength of 555 millimicrons via a three millimeter pupil should form the first dark ring with an angular subtense of about 47 arc seconds or about 0.004 millimeters in diameter. This figure agrees well with the observed packing density of receptor cells in the fovea and provides a definition of best contour acuity in the "normal" ametropic eye. However, there is also the phenomenon of "vernier acuity" which defines the ability to see a discontinuity in a line. This is much smaller and is influenced by the time of observation so we may conclude that some averaging is taking place in the visual processing system of the brain.

Referring now to the cross sectional view of the preferred embodiment, FIG. 9, the reticle projection system comprises a lamp 45, a condenser lens 24, an apodizing filter 48, a reticle 47 and a projector lens 2. The image of the reticle 47 is focused on the eye 1 and when the lamp 45 flashes, the plurality of illuminated points so produced on the cornea of the eye 1 produces a plurality of Tyndall images which contain not only surface contour information but also corneal thickness information. A small display 49 such as is used for a viewfinder on small videotape cameras is made viewable through a lens 21 for providing the operator a television image from the central camera suitable for performing the centering, focus and Purkinje image alignment steps. The television images from the cameras 4 are again captured and stored for analysis, as described above.

The pseudo-placido disc is constructed in the conventional manner except that in lieu of a set of concentric circles of translucent material, the pattern is divided into a plurality of circular translucent areas arranged in concentric circles. The illuminated spots to be reflected by the cornea are sized to provide five or more pixels of subtense in the captured image with a separation of at least twice the illuminated diameter. These provide a basis for accurate back tracing the rays without the ambiguity inherent in a continuous circular form of Placido rings of the prior art to eliminate one of the error sources of those devices. Analysis of the isolated points produced in the image subtraction step produces a large number of locations on the corneal surface for which the surface slope is known. The projected image of the reticle is distorted by the surface slope of the cornea at the point of the projected spots and the Placido derived data are then used to define and eliminate this distortion from the reticle projection derived images. The spots as so derived are not circular due to the diffuse reflection within the bulk of the cornea but with the surface shape induced distortion removed, the centroids of the "blob" can be accurately defined to provide the basis for definition of the local corneal thickness.

Triangulation from the plural images produced by the projection system provides an accurate method for defining the now central corneal apex by the action of Purkinje image alignment. This, in turn, provides the vital but missing information from the Placido based systems of the prior art to significantly enhance the accuracy of the surface contour data derived from the Placido reflection step and this, in turn, provides a more accurate data base for analysis of the pachymetric and contour data derived from the reticle projection system.

Thus, there has been disclosed a method and apparatus for measuring corneal shape and thickness. The method and apparatus of the invention for measuring corneal contour and thickness can be applied to clinical procedures, particularly contact lens fitting. The foregoing descriptions of a number of embodiments of the present invention are representative of the techniques employed and these descriptions are not intended as a limit on the scope of the invention. It will be obvious to one skilled in the art that various changes and modifications may be made and all such changes and modifications are considered to be within the scope of the invention as defined by the appended claims.

Having thus described the invention, what I desire to claim and secure by Letters Patent is:

1. An instrument for measuring surface shape and thickness of a cornea for clinical diagnostic purposes comprising:
   a) an optical projector which projects a pattern of isolated points on the cornea;
   b) an illuminated target that can be reflected from said cornea, said pattern comprising a plurality of isolated points;
   c) camera means comprising a camera array and detector array, said camera means being aligned to intersect in a common point located slightly beyond said cornea, said camera means also producing a plurality of sequential images of said cornea;
   d) a computer receiving the electrical analog of the images from said camera means; and
   e) means utilizing the electrical analog of said images for defining the surface contour and for defining the thickness of said cornea from at least said projected points and reflected image points.

2. The instrument of measuring surface shape and contour of claim 1 further characterized in that said camera means comprises at least three cameras, two of said cameras disposed at equal angles to the axis of projection of said projector, and a third camera for forming an image of the eye located centrally with an optical axis coincident with the said projector.

3. The instrument of measuring surface shape and contour of claim 20 further characterized in that said cameras are provided with timing means to assure temporal synchronism between all of said cameras.

4. The instrument of measuring surface shape and contour of claim 1 further characterized in that said instrument comprises sequencing means for controlling the illumination of the eye indirectly and with the projected and reflected patterns disposed on the cornea sequentially.

5. The instrument of measuring surface shape and contour of claim 1 further characterized in that said instrument comprises an illuminated target disposed for viewing by the subject of examination through the centrally located camera lens, said target being movable in the focal plane of the said lens perpendicular to the axis of view for establishing a desired relationship between the several reflections of the said target.

6. The instrument of measuring surface shape and contour of claim 1 further characterized in that said computer comprises means for isolating the images of each of the reflected points and projected points.

7. The instrument of measuring surface shape and contour of claim 6 further characterized in that said computer establishes the location in three dimensions of each of the said plurality of image or reflecting points by triangulation.

8. The instrument of measuring surface shape and contour of claim 7 further characterized in that the means for defining surface contour and thickness defines the surface contour and thickness of the said cornea from the said projected and reflected image points.

9. The instrument of measuring surface shape and contour of claim 1 further characterized in that the instrument comprises a display for displaying the surface and thickness information of the cornea.

10. A method for measuring surface shape and thickness of a cornea for clinical diagnostic purposes, said method comprising:
   a) projecting a pattern of isolated points on said cornea;
   b) reflecting from said cornea said pattern;

c) producing a plurality of sequential images of the said cornea from a camera means;

d) receiving the electrical analog of the images from said camera means;

e) isolating the images of each of the plurality of reflected and projected points; and f) defining the surface contour and thickness of the said cornea from the said projected and reflected image points.

11. The method of claim 10 further characterized in that said method comprises producing the sequential images from a plurality of cameras which comprises said camera means with each comprising a camera array and detector array, two of said cameras disposed at equal angles to the axis of projection of the said projector, and a third camera for forming an image of the eye located centrally with an optical axis coincident with the said projector.

12. The method of claim 11 further characterized in that said method comprises assuring temporal synchronism between all of the said cameras, and alignment of the optical axes of the said cameras aligned to intersect in a common point located slightly beyond said cornea.

13. The method of claim 10 further characterized in that the method comprises controlling the illumination of the eye indirectly and with the projected and reflected patterns disposed on the cornea sequentially with a sequencing means.

14. The method of claim 10 further characterized in that said method comprises establishing by triangulation the location in three dimensions of each of the said plurality of image or reflecting points.

15. The method of claim 10 further characterized in that said method comprises displaying the surface and thickness information of the cornea.

16. A hand-held keratometer/pachymeter device capable of measuring a surface shape and a thickness of a cornea for diagnostic purposes, said device comprising:

a) an outer housing;

b) light generating means within said housing for projecting a pattern of isolated points on the cornea of an eye being examined;

c) camera means located within said housing and being arranged to be aligned with the cornea and intersect at a common point behind the cornea and thereby produce a plurality of sequential images thereof;

d) an eyepiece on said housing located in a position which is distant to the axis of said camera means;

e) an optical path including optical elements for causing an image of reflected isolated points on the cornea to be directed to said eyepiece; and f) means associated with said housing for defining the surface contour and thickness of the cornea from the projected and reflected image points.

17. The keratometer/pachymeter device of claim 16 further characterized in that said housing includes a handle for grasping by the hands of a user making the corneal shape and thickness measurements.

18. The keratometer/pachymeter device of claim 17 further characterized in that said handle is a pistol-grip type handle and that said housing includes a chin support extending forwardly thereof.

19. The keratometer/pachymeter device of claim 16 further characterized in that said housing includes a battery source of power for operation thereof.

20. The keratometer/pachymeter device of claim 16 further characterized in that said a fixation target is mounted within said housing and generates a light path with respect to said optics for viewing by a subject of examination.

21. A keratometer/pachymeter device for measuring surface shape and thickness of a cornea for clinical diagnostic purposes, said device comprising:

a) means for projecting a pattern of isolated points on the cornea of an eye being tested;

b) target means for reflecting from the cornea a plurality of reflected isolated points;

c) means for generating electrical signals representative of the reflected isolated points and the projected isolated points; and d) means for defining the surface contour and the thickness of the cornea from those projected points and reflected image points.

22. The instrument of claim 21 further characterized in that an optical projector is used to project isolated points.

23. The instrument of claim 21 further characterized in that a plurality of cameras are arranged to produce sequential images of the cornea using the isolated and reflected points.

24. The instrument of claim 21 further characterized in that the instrument comprises a sequencing means for controlling the illumination of the eye with both projected and reflected patterns of points.

25. A method of ascertaining corneal contour and thickness using a combination of pachymetry and keratometry comprising:

a) projecting an array of illuminated points in concentric circles around an optical axis for definition of surface contour;

b) providing back trace information from the isolated point ring to provide Tyndall images representative of the definition of both anterior and posterior corneal surface;

c) using triangulation with the reflected images and the Tyndall images; and d) using each of the patterns of images in sequence for isolation of data from background pictorial information.

* * * * *